(12) United States Patent
Meadows et al.

(10) Patent No.: US 9,006,272 B2
(45) Date of Patent: Apr. 14, 2015

(54) PHARMACEUTICAL COMPOSITIONS AND METHOD FOR TREATING INFLAMMATION IN CATTLE AND OTHER ANIMALS

(75) Inventors: Cheyney Meadows, Peapack, NJ (US); Keith A. Freehauf, Stockton, NJ (US); Robert D. Simmons, Martinsville, NJ (US); Allan J. Weingarten, Westfield, NJ (US)

(73) Assignee: Intervet Inc., Madison, NJ (US)

( * ) Notice: Subject to any disclaimer, the term of this patent is extended or adjusted under 35 U.S.C. 154(b) by 1756 days.

(21) Appl. No.: 11/959,185

(22) Filed: Dec. 18, 2007

(65) Prior Publication Data

US 2008/0153885 A1     Jun. 26, 2008

Related U.S. Application Data

(60) Provisional application No. 60/870,907, filed on Dec. 20, 2006.

(51) Int. Cl.
| | | |
|---|---|---|
| *A61K 31/44* | (2006.01) | |
| *A61P 29/00* | (2006.01) | |
| *A61K 9/00* | (2006.01) | |
| A61K 47/06 | (2006.01) | |
| A61K 47/10 | (2006.01) | |
| A61K 47/14 | (2006.01) | |
| A61K 47/16 | (2006.01) | |
| A61K 47/20 | (2006.01) | |

(52) U.S. Cl.
CPC .............. *A61K 31/44* (2013.01); *A61K 9/0017* (2013.01); *A61K 47/06* (2013.01); *A61K 47/10* (2013.01); *A61K 47/14* (2013.01); *A61K 47/16* (2013.01); *A61K 47/20* (2013.01); *Y10S 514/947* (2013.01)

(58) Field of Classification Search
None
See application file for complete search history.

(56) References Cited

U.S. PATENT DOCUMENTS

2003/0175331 A1 *  9/2003  Sasaki et al.
2007/0117828 A1     5/2007  Simmons et al.

FOREIGN PATENT DOCUMENTS

| JP | 11-222443 | * | 8/1999 |
| WO | 01/35883 A1 | | 5/2001 |
| WO | 2005/009436 A1 | | 2/2005 |
| WO | 2005/009510 A2 | | 2/2005 |

OTHER PUBLICATIONS

Kemerling, Louisiana State University Equine Veterinary Research Program Newsletter, "Non Steroidal Anti-inflammatory Drugs (NSAIDs) Affect Pain and Inflammation", 1997, pp. 1-6 of 6.*
Thomasy et al., Journal of Veterinary Internal Medicine, 2004, vol. 18(4), pp. 550-554; abstract only.*
FDA Supplemental Abbreviated New Animal Drug Application, ANADA 200-124, Jul. 18, 2005, pp. 1-5 of 5, downloaded on May 31, 2014 from "http://www.fda.gov/downloads/AnimalVeterinary/Products/ApprovedAnimalDrugProducts/FOIADrugSummaries/ucm061738.pdf".*
International Search Report for Corresponding application PCT/US29007/025808, mailed Jan. 20, 2009.

* cited by examiner

*Primary Examiner* — Savitha Rao
*Assistant Examiner* — Gregg Polansky

(57) ABSTRACT

Novel transdermal preparations combining a non-steroidal anti-inflammatory drug (NSAID) such as flunixin, are disclosed. Methods for using and administering such preparation in the treatment of inflammatory conditions in bovines, including bovine respiratory disease, are also disclosed.

17 Claims, 5 Drawing Sheets

PHARMACEUTICAL COMPOSITIONS AND METHOD FOR TREATING INFLAMMATION IN CATTLE AND OTHER ANIMALS

This application claims the benefit of U.S. Provisional Application No. 60/870,907, filed Dec. 20, 2006

FIELD OF THE INVENTION

The present invention relates to compositions and methods for the treatment of inflammation in animals. More particularly, the invention relates to transdermal administration of a non-steroidal anti-inflammatory drug (NSAID) in animals.

BACKGROUND OF THE INVENTION

All patents, applications, publications, test methods, and other materials cited herein are incorporated by reference.

Inflammation is a process that occurs in response to injury or other abnormal stimulation by physical, chemical, or biological agents, with the purpose of helping to overcome the abnormal stimulus. Inflammation involves local tissue reactions and morphologic changes, destruction or removal of injurious material, and the initiation of repair and/or healing. Cardinal signs of active inflammation include redness, heat, swelling, pain, and reduction or loss of function; these signs can present locally and/or systemically.

While the purpose of an inflammatory response is to help the host overcome an abnormal stimulus, inflammatory episodes can have deleterious effects. In the short-term, febrile or painful animals may have reduced feed and water intake, which can create the risk of developing problems related to a negative energy balance or dehydration. Furthermore, some inflammatory episodes can leave long-lasting residual damage, scarring, and reduced functionality.

For example, bovine respiratory disease (BRD) occurs in both dairy and beef cattle and is one of the leading causes of economic loss to the cattle industry throughout the world. Economic losses are attributable to excessive mortality, treatment and prevention costs, and decreased productivity—dairy cattle with clinical or sub-clinical BRD do not gain weight or produce milk as well as healthy animals, and beef cattle with BRD gain less weight, have reduced feed efficiency and often produce a lower grade carcass at slaughter. A direct correlation between pulmonary lesions observed at slaughter and reduced weight gains has been established in cattle with sub-clinical BRD infections. The etiologic agents of BRD are bacterial organisms such as *Mannheimia haemolytica, Pasteurella multocida* and *Histophilus somni*. However, in BRD infections, the pulmonary damage that results in death or morbidity is often due to an excessive host inflammatory response to the invading pathogens. In the short term, febrile, painful animals eat and drink less. Furthermore, long-term damage to host tissues occurs, resulting in long-term declines in productivity even after BRD infection has resolved.

Bovine mastitis is considered to be the most costly production disease faced by the dairy industry, costing hundreds of millions of dollars per year. Bovine mastitis is typically caused by infectious agents such as *Staphylococcus aureus, Streptococcus* species, and *Escherichia coli*. In response to infection, the mammary gland undergoes an inflammatory process, characterized by warmth, pain, redness, swelling, and impaired function. The affected animal often develops a fever and eats and drinks less. There is a transient decrease in milk production during the acute inflammatory stage, and subsequent milk yield for the remainder of the lactation is reduced as a result of residual inflammatory damage.

In addition to cattle, other species are similarly susceptible to short-term and long-term effects of inflammatory episodes induced by a variety of causes. Regardless of species or causative agent, the damage brought about by inflammation evolves as neutrophils and other inflammatory cells destroy affected tissues. As cell membranes are damaged, arachidonic acid is released. Arachidonic acid is the substrate for the formation of various prostaglandins and other eicosanoids. The release of these biologically active substances is critical to driving the inflammatory response that results in additional inflammatory damage and lesions. Non-steroidal anti-inflammatory drugs (NSAIDs) effectively modulate inflammation by disrupting the arachidonic acid cascade.

Use of NSAIDs is a cornerstone of management of inflammatory processes in human and veterinary medicine. Regardless of the species or organ system affected or the cause, pharmacologic modulation of inflammation offers important quality of life benefits to painful or febrile animals, allowing the affected animal to eat and drink and thus increase the potential for recovery. Furthermore, use of NSAIDs helps to reduce excessive damage that results in long-term reduction of functionality, thus bringing economic benefits to livestock producers.

Flunixin megiumine is the active ingredient in FINA-DYNE® and BANAMINE® (both available from Schering-Plough Animal Health Corporation). It has emerged as one of the leading NSAIDs in large animal veterinary medicine and is a first choice NSAID for adjunctive therapy of BRD and mastitis in cattle. Flunixin meglumine has been studied extensively in regard to its use in conjunction with antibiotics for the treatment of BRD and mastitis.

Both flunixin meglumine and flunixin base both have very poor lipid solubility. Traditionally, a compound needs to have a moderate degree of lipid solubility in order to be delivered across the lipid layers of the skin. Because of the undesirable solubility characteristics of flunixin meglumine, it presents challenges regarding formulating it into an effective transdermal liquid preparation.

Flunixin meglumine is currently formulated for intravenous injection in cattle using a syringe and needle, which introduces some challenges. Needles present challenges with respect to accumulation and disposal of sharp biowaste material, needle stick hazards for human handlers, and an additional discomfort for animals being treated. Also, the requirement for intravenous injection requires some technical expertise for proper administration. As a result of these requirements for proper administration of flunixin meglumine to cattle, some animals in need may go untreated in the interest of reducing needle waste, protecting human handlers, or because of technical limitations.

Thus, there is a need for an improved formulation and method of administration, such as a formulation for transdermal drug delivery, which addresses these problems. One difficulty faced, however, when attempting to arrive at a transdermal formulation is the fact that the skin has been described as a "black box" with regard to drug delivery. This is due to the lack of knowledge in the mechanisms of drug penetration through the epidermis and partitioning into the underlying layers. Thus far, the boundaries for such properties have not been defined; making it very difficult to predict what compounds can be delivered transdermally. Transdermal systems effective for delivering one compound are almost always ineffective with other compounds and systems and devices that work in one species are almost universally ineffective in other species. Furthermore, due to the presence of stratum corneum barrier, the mass transfer through the skin is usually too slow for rapid, massive systemic absorption. This explains why very few, if not any, of the commercially available transdermal products for human use are designed for immediate drug delivery.

Accordingly, there is a need for stable, transdermal liquid preparation that offers a way for handlers to safely and conveniently administer flunixin to animals in need thereof to ameliorate inflammation, while minimizing the pain and stress to the animal associated with treatment and the potential for injection site tissue damage.

SUMMARY OF THE INVENTION

The present invention fulfills this need by providing improved preparations and methods for the delivery of flunixin and other NSAIDs in cattle and other animals.

Accordingly, there are disclosed pharmaceutically acceptable preparations for transdermal administration to animals and methods for the use thereof. Such preparations comprise flunixin or a pharmaceutically acceptable salt thereof, a pharmaceutically acceptable carrier system comprising a solvent system and a combination of two penetration enhancing agents. In optional aspects of the invention, the transdermal liquid preparations can include a stabilizing or viscosity lowering agent, such as water, ethanol, isopropanol, propylene glycol, dimethylisosorbide, or triacetin.

One preferred aspect of the invention includes a transdermal liquid preparation containing:

a) flunixin or a pharmaceutically acceptable salt thereof;
b) a first and a second dermal penetration enhancer; and
c) one or more aprotic primary solvents.

In a second preferred aspect of the invention, one or more additional solvents or carriers (referred to herein as "second" or "secondary" solvents or vehicles) can also be included in the transdermal liquid preparation.

Within the first and second aspect of the invention, the first dermal penetration enhancer can be present in an amount from about 2% to about 20% of the transdermal liquid preparation, while the second dermal penetration enhancer can be present in an amount from about 2% to about 50% of the transdermal liquid preparation. In particular, one first dermal penetration enhancer is menthol, while xylene, D-limonene, isopropyl myristate, propylene glycol dicaprylate/dicaprate, decanoic acid, decyl alcohol, oleic acid, or mixtures thereof are particular examples of second dermal penetration enhancers.

The amount of the drug included in the transdermal liquid preparations described herein can be present in an amount from about 1 to about 20% by wt. (calculated on the basis of the flunixin free acid), while the amount of the aprotic primary solvent can broadly be from about 5 to about 90% by wt. In particular, aprotic primary solvents useful in the present invention are 2-pyrrolidone, N-methyl-2-pyrrolidone, ethyl lactate, and glycol ethers such as ethylene glycol monoethyl ether, diethylene glycol monoethyl ether, or dipropylene glycol monoethyl ether, while particular examples of secondary solvents include ethanol, isopropyl alcohol, and benzyl alcohol.

In another aspect of the invention, there are provided methods of treating inflammatory conditions. Some of these methods include administering an effective amount of a transdermal preparation as described above to an animal, like a mammal such as a bovid (e.g. cow) in need thereof.

The present composition can also optionally include other NSAIDs besides flunixin, as well as other active pharmaceutical ingredients such as anti-microbials, hormones for reproduction, growth enhancement, or other physiologic intervention, anxiolytic compounds, antihistamines, immune stimulants, vaccines and the like, for example.

In another aspect of the invention, there are provided methods of administering the transdermal flunixin liquid preparation comprising incorporating the transdermal liquid preparation into a press-in bottle application device, and administering an effective amount of the transdermal liquid preparation to an animal in need thereof.

With the foregoing and other objects, advantages and features of the invention that will become apparent hereinafter, the nature of the invention may be more clearly understood by reference to the following detailed description of the invention and the appended claims.

DETAILED DESCRIPTION OF THE INVENTION

Figure 1:
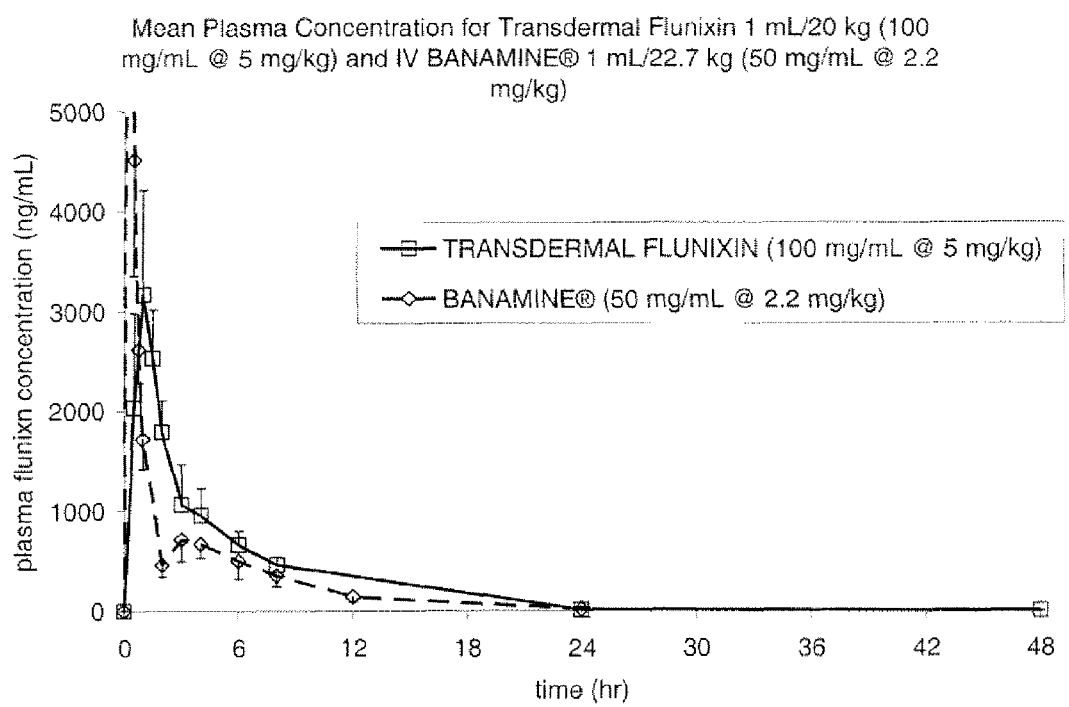
FIG. 1 is a graph showing the results of the tests carried out in Example 2, in which the mean plasma concentration (−1 SD) of flunixin (free acid) vs. time after a single 2.2 mg/kg IV dose of Banamine® (flunixin megiumine) (diamonds connected by dotted line) is compared to a single 5 mg/kg transdermal dose of composition of the present invention (+1 SD, squares connected by solid line).

It has been found that effective concentrations of flunixin or pharmaceutically acceptable salts thereof in the systemic circulation for the purpose of providing systemic anti-inflammatory activity can be achieved by the transdermal route of administration. This can encompass various types of delivery including pour-on, spot-on, spray, dip, wipe, etc.

The present invention relates to an NSAID product for providing systemic anti-inflammatory (including anti-pyrexia and analgesia) activity for animals, especially mammals such as cows. The present invention demonstrates that, through improved compositions and methods of delivery, flunixin can effectively diffuse through the skin and further partition into the underlying layers for rapid absorption. It was discovered that the pharmacokinetic parameters of the present invention are comparable to those obtained by the counterpart intramuscular injectable formulations. The high Cmax and the short Tmax values obtained suggest sufficient drug cargo was carried through the skin barrier with high flux. The high area under the time-plasma concentration curve (AUC) indicates complete absorption of the active into the systemic circulation. The pharmacokinetic data shows high efficiency of skin barrier penetration, as well as tissue partitioning from the current formulations.

It has also been discovered that when selected penetration enhancing agents are used together, they function synergistically to provide increased systemic activity. In fact, the combination of two penetration enhancing agents is demonstrated to be significantly superior to the use of a single penetration enhancing agent alone. The compositions of the present invention can be used to prevent or reduce inflammation associated with an infectious disease, surgery, injury, or other cause.

As used herein, the following terms, unless otherwise indicated, shall be understood to have the following meanings:

"transdermal application" and/or "transdermal liquid preparation" is intended to encompass all such methods known for allowing a pharmaceutically active ingredient to be delivered at least partially through the skin, usually by applying the composition containing the active ingredient and formulation excipients externally to the surface, i.e. skin, fur, etc. of an animal and allowing sufficient time for absorption through the dermal layers of the animal being treated. Methods of administration include pour-on, spot-on, spray, dip, wipe, or other methods apparent to those skilled in the art;

"pour-on" is intended to encompass routes of administration in which an effective amount of a suitable pharmaceutically active ingredient is externally applied to a localized region, allowing for diffusion of an effective amount of the pharmaceutically active ingredient to the affected area(s) or systemic distribution or a region which will facilitate delivery of the pharmaceutically active ingredient to the affected area(s) or systemic distribution;

"composition" "formulation" and/or "preparation" is intended to encompass a product comprising the specified ingredients disclosed herein in the specified amounts disclosed herein, as well as any product which results, directly or indirectly, from combination of the specified ingredients disclosed herein in the specified amounts disclosed herein; and an "effective amount" is a dose required to alleviate a particular symptom of an infection or disease.

In accordance with a first aspect of the invention, the transdermal liquid preparation contains a therapeutically effective amount of flunixin or a pharmaceutically acceptable salt thereof, a first and a second dermal penetration enhancer, and an aprotic primary solvent.

In the formulations of the invention, the concentration of flunixin can be from about 1 to about 20% by weight of the transdermal liquid preparation (based on the free acid content of flunixin), or particularly from about 5% to about 15% by weight, or particularly with amounts being from about 7.5% to about 12.5%, or particularly with amounts being from about 9 to about 11% by weight. The flunixin can be introduced into the formulation as a pharmaceutically acceptable salt, in which case the concentration of the salt would be adjusted in order to maintain the preferred flunixin concentration.

The pharmaceutically acceptable salt of flunixin is preferably flunixin meglumine. Flunixin meglumine is currently approved globally for use in the treatment of BRD and mastitis. It has become a mainstay of veterinary practice for the treatment of inflammatory conditions. Flunixin meglumine is commercially available from, e.g., ISP (Wayne, N.J.), or may be made according to methods known in the art, e.g., the methods described in U.S. Pat. Nos. 3,337,570, 3,478,040 and 3,839,344.

The transdermal liquid preparation of the invention also includes a first dermal preparation enhancer. In particular embodiments of the invention, the first dermal penetration enhancer is present in amounts from about 2 to about 20% w/v of the transdermal liquid preparation, particularly from about 5 to about 15% w/v or particularly from about 7.5 to about 12.5% w/v.

Non-limiting examples of a suitable first dermal preparation enhancer include, but are not limited to, terpenoids such as menthol, camphor, d-limonene, nerolidol, 1-8 Cineole and mixtures thereof. Particularly, the first dermal penetration enhancer is menthol and is employed in an amount of 10% w/v.

A second dermal preparation enhancer is also present in the transdermal liquid preparation of the invention. The second dermal penetration enhancer is particularly present in an amount from about 2 to about 50% w/v of the transdermal liquid preparation, particularly from about 5 to about 30% w/V, or particularly from about 7.5 to about 12.5% w/v.

Non-limiting examples of a suitable second dermal preparation enhancer include, but are not limited to, a second terpenoid, saturated or unsaturated fatty acid esters or diesters of propylene glycol or glycerol, saturated or unsaturated fatty acids, saturated or unsaturated fatty alcohols and mixtures thereof.

Particularly, the second dermal penetration enhancer is employed in an amount of 10% w/v and is xylene, D-limonene, isopropyl myristate, propylene glycol dicaprylate/dicaprate, decanoic acid, decyl alcohol, oleic acid or mixtures thereof. Particularly, the second dermal penetration enhancer is propylene glycol dicaprylate/dicaprate and/or xylene and/or D-limonene and/or isopropyl myristate.

In one particular formulation of the invention, the first dermal penetration enhancer is menthol, and the second dermal penetration enhancer is propylene glycol dicaprylate/dicaprate and/or xylene and/or D-limonene and/or isopropyl myristate.

Particularly, the ratio of the first dermal penetration enhancer to the second dermal penetration enhancer is from about 4:1 to about 1:4.

It has been discovered that the combination of the first and second dermal penetration enhancers provides a synergistic increase in the systemic availability of flunixin or its pharmaceutically acceptable salt compared to the use of a single penetration enhancer alone. As described, and, for example, in Example 6 and illustrated in FIG. 3, the plasma uptake of flunixin is significantly enhanced when a first dermal penetration enhancer (menthol in Example 6) is employed in combination with a second dermal penetration enhancer (xylene in Example 6).

The transdermal liquid preparation of the invention also includes an aprotic primary solvent. In particular formulations of the invention, the aprotic primary solvent is present in an amount from about 5 to about 90% by weight of the transdermal liquid preparation, particularly, from about 10 to about 60% by weight, or particularly from about 20 to about 50% by weight.

Non-limiting examples of a suitable aprotic primary solvent include, but are not limited to, aprotic solvents such as a pyrrolidone solvent, such as 2-pyrrolidone, N-methyl-2-pyrrolidone, and/or mixtures thereof, N,N-dimethylacetamide, N,N-dimethylformamide, DMSO, acetone, glycerol formal, ethyl lactate, and glycol ethers such as ethylene glycol monoethyl ether, diethylene glycol monoethyl ether, or dipropylene glycol monoethyl ether, or mixtures thereof. Particularly, the aprotic primary solvent is 2-pyrrolidone, N-methylpyrrolidone, mixtures thereof and the like.

Other pharmaceutically acceptable secondary vehicles or solvents may be present in the formulations of the present invention. Non-limiting examples of suitable secondary vehicles or solvents include, but are not limited to, water, ethanol, isopropanol, 1,2-propanediol, glycerin, benzyl alcohol, dimethylisosorbide, triacetin, propylene glycol, ethyl lactate, glycol ethers such as ethylene glycol monoethyl ether, diethylene glycol monoethyl ether, or dipropylene glycol monoethyl ether, and polyethylene glycols (PEG) having an average molecular weight between about 200 and 400. In particular, secondary vehicles or solvents include isopropyl alcohol, benzyl alcohol, and PEG having an average molecular weight between about 200 and about 400, triacetin, dimethylisosorbide, ethanol, and water, and combinations thereof. These secondary vehicles or solvents may comprise up to about 80% by weight of the formulation. The secondary vehicles or solvents may comprise from about 10% to about 75% by weight. Particularly, the secondary vehicles or solvents comprise from about 20% to about 40% by weight of the formulation.

The addition of one or more of such secondary vehicles or solvents may be desirable to alter the viscosity of the formulation in order to provide a product with appropriate characteristics for transdermal application.

The transdermal liquid preparation of the invention can also optionally include a second pharmaceutically active compound, or other therapeutic classes of drugs such as antimicrobials, anti-inflammatory agents, oxytocin, hormones for reproduction, growth enhancement compounds, physiologic intervention compounds, anxiolytic compounds, antihistamines, immune stimulants, and vaccines and the like, for example. As will be appreciated by those of ordinary skill, a wide variety of pharmaceutically active compounds/agents can be included with the flunixin-based transdermal formulations described herein. The only limitation on the type of pharmaceutical agent which can be included is that the second agent must not significantly interact with or significantly diminish the activity of the flunixin or pharmaceutically acceptable salt being transdermally administered.

A non-limiting list of suitable pharmaceutically active compounds include those falling in the categories of anti-inflammatory agents, such as NSAIDs and corticosteroids, antibiotics, anti-pyretics, analgesics, etc. and the like. In one particular aspect, the transdermal formulations will include an antibiotic such as a fluorine-containing analog of the antibiotics chloramphenicol and thiamphenicol, which have been shown to have antibiotic activity both against organisms sensitive to and resistant to chloramphenicol and thiamphenicol. See Schafer, T. W. et al., "Novel Fluorine-Containing Analogs of Chloramphenicol and Thiamphenicol: Antibacterial and Biological Properties," in CURRENT CHEMOTHERAPY AND INFECTIOUS DISEASE PROCEEDINGS OF THE 11.sup.TH ICC AND THE 19.sup.TH ICAAC AMERICAN SOCIETY OF MICROBIOLOGY 1980, 444-446. Examples of such compounds, and methods for their manufacture, are described and claimed in U.S. Pat. No. 4,235,892.

Suitable NSAIDs, include, without limitation, acemetacin, acetylsalicylic acid (aspirin), alminoprofen, benoxaprofen, bucloxic acid, carprofen, celecoxib, clidanac, deracoxib, diclofenac, diflunisal, dipyrone, etodolac, fenoprofen, fentiazac, firocoxib, flobufen, flufenamic acid, flufenisal, flunixin, fluprofen, flurbiprofen, ibuprofen, indomethacin, indoprofen, isoxicam, ketoprofen, ketorolac, meclofenamic acid, mefenamic acid, meloxicam, miroprofen, nabumetone, naproxen, niflumic acid, oxaprozin, oxepinac, phenylbutazone, piroxicam, pirprofen, pramoprofen, sudoxicam, sulindac, suprofen, tepoxalin, tiaprofenic acid, tiopinac, tolfenamic acid, tolmetin, trioxaprofen, zidometacin, or zomepirac, pharmaceutically acceptable salts thereof and mixtures thereof. However, particularly preferred is flunixin because a history of safe and effective use in BRD and mastitis has been established. Suitable animicrobials include, but are not limited to, compounds from classes such as aminoglycosides, beta-lactams, cephalosporins, floroquinolones, lincosamides, macrolides, sulfonamides and potentiated sulfonamides, tetracyclines, and fluorine-containing analogs of chloramphenicol. Suitable growth enhancing agents include, without limitation, somatotropin and zeranol. Suitable anxiolytic compounds include, without limitation, NOP-1 receptor agonists, NK-1 receptor antagonists, benzodiazepines, and phenothiazines. Suitable antihistamines include, without limitation, diphenhydramine and tripelennamine.

Other ingredients can be added to the present composition, as desired. Such ingredients include preservatives, chelating agents, antioxidants, and viscosity modifying agents. Exemplary preservatives include without limitation methyl p-hydroxybenzoate (methylparaben) and propyl p-hydroxybenzoate (propylparaben), added in an appropriate quantity known to one skilled in the art. Exemplary chelating agents include without limitation edetate disodium and EDTA. Exemplary antioxidants include without limitation butylated hydroxyanisole, ascorbic acid, and sodium monothioglycerol, added in an appropriate quantity known to one skilled in the art. Suitable viscosity modifying agents include, without limitation, water, ethanol, isopropanol, propylene glycol, dimethylisosorbide, triacetin, or glycerol, added in an appropriate quantity known to one skilled in the art.

In order to prevent degradation of any of the active ingredients in the formulations of the present invention, the addition of at least one stabilizer has been found to be advantageous. Citric acid and maleic acid are examples of stabilizers useful in the present invention.

In order to prevent degradation of any of the active ingredients in the formulations of the present invention, a pH adjusting agent has been found to be advantageous.

The amount of the active agent(s) or any other excipients may be varied to after the dose volume delivered or the physical properties of the formulation. The amount of the second pharmaceutically or therapeutically active agent will depend on transdermal bioavailability and pharmacologic synergy with other actives in the formulation and will be titrated to effect.

In some particular embodiments, the transdermal formulations in accordance with the invention have a similar plasma profile to that observed with injectable Banamine® (flunixin meglumine) (a short onset of activity and clearance from plasma within 24 hours). Because the formulations of the invention have a short onset of activity, animals will benefit from rapid relief of clinical signs. Also, because the formulations of the invention clear from plasma within 24 hours, shorter withhold times will be required prior to selling milk or meat from treated animals.

It will also be appreciated that the present invention encompasses, in one aspect, methods of treating inflammation by administering, for example, a pharmaceutically acceptable composition comprising, for example, flunixin or a pharmaceutically acceptable salt thereof, to an animal by transdermal administration. The composition can be applied in a variety of ways, such as a pouring, spraying, or wiping on to any area of the animal's skin, including the back, ears, or udder, preferably the back. The amount of administered flunixin or its pharmaceutically acceptable salt is from about 1 to about 5 mg/kg flunixin active.

Figure 5:
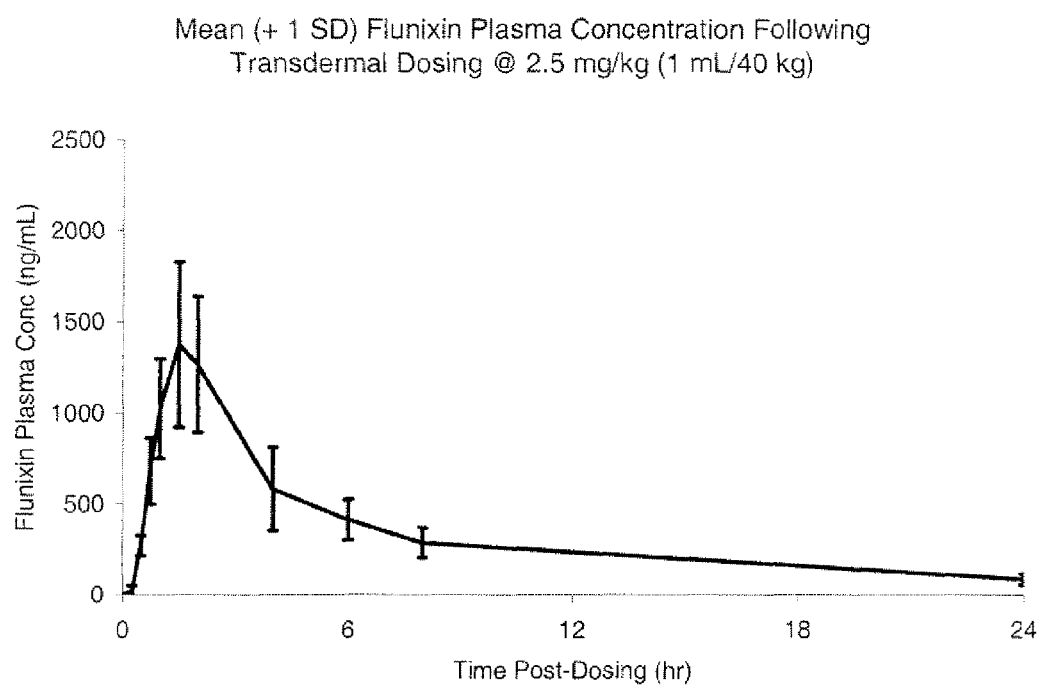
FIG. 5 is a graph showing the results of the tests carried out in Example 8, in which the mean plasma concentration (±1 SD) of flunixin (free acid) vs. time after a single 2.5 mg/kg transdermal dose of composition of the present invention.

Formulation efforts on the product of the invention were directed at creating a pharmacokinetic profile for flunixin or its pharmaceutically acceptable salts following transdermal applications to be as similar as possible to that observed for Banamine® injectable. A formulation containing 100 mg/mL of flunixin was developed and transdermally administered at a dose of 5 mg/kg of flunixin. The data presented in FIG. 1 demonstrated that the flunixin plasma profile is similar to that of a known effective profile. For example, plasma concentrations of flunixin, following a single transdermal administration of about 5 mg/kg of flunixin achieved a Cmax of greater than 3000 ng/ml at a Tmax of about 60 minutes. The data presented in FIG. 5 show the plasma profile following transdermal administration at a dose of 2.5 mg/kg of flunixin. Following a single transdermal dose of 2.5 mg/kg, a Cmax of about 1500 ng/mL was achieved at a Tmax of about 90 minutes. In this example (FIG. 5), the bioavailability of the flunixin transdermal solution was greater than 50%.

The present invention also includes a transdermal composition for the treatment of inflammatory conditions in an animal. Particularly, the transdermal composition comprises from about 5% to about 15% by wt of a first dermal penetration enhancer, from about 2% to about 50% by wt of a second dermal penetration enhancer, from about 5% to about 15% of flunixin or a pharmaceutically acceptable salt thereof based on the free acid content of flunixin, from about 5% to about 90% of an aprotic primary solvent; and up to about 80% of a second vehicle or solvent, wherein the transdermal composition exhibits with respect to flunixin a Cmax of from about 1600 to about 4800 ng/mL, and a Tmax of from about 30 minutes to about 2 hours when administered transdermally to bovids at a flunixin dose of about 5 mg/kg. The transdermal composition exhibits with respect to flunixin a Cmax of from about 1000 to about 2500 ng/mL, and a Tmax of from about 60 minutes to about 2 hours, and a bioavailability of greater than 50% when administered transdermally to bovids at a flunixin dose of about 2.5 mg/kg.

In addition to greater convenience and ease of use, it is believed that a single daily administration of a transdermal product in accordance with the present invention will promote humane animal care by reducing the number of injections needed to treat animals and providing rapid relief of disease symptoms. By reducing the number of injections, manpower costs also may be significantly reduced.

In a particular method of preparing the composition of the present invention, the vehicle(s) or a portion of the vehicle(s), are added to the compounding vessel, followed by the remaining excipients and the actives. The mixture is mixed until all solids are dissolved. An additional solvent to bring the composition to final volume may be added if needed. Additives, such as those listed above, may also be included in the vessel and mixed into the formulation. The order of addition of the above vehicles, excipients, solvents and additives is not critical.

The compositions according to the present invention will generally be administered to cattle at from about 1 mg to about 5 mg of flunixin per kilogram of body weight per day. Particularly, the compositions of the present invention will be administered to cattle at about 2.5 mg of flunixin per kilogram of body weight.

The compositions may be administered once daily or divided into multiple doses. In some circumstances, daily doses will be required to treat the animal. The precise dose will depend on the stage and severity of the condition being treated, and the individual characteristics of the animal species being treated, as will be appreciated by one of ordinary skill in the art.

The compositions of the present invention may be administered in a press in bottle insert application device (PIBA) to an animal in need thereof. Such a device allows a health care professional to easily dispense liquids from stock bottles into (oral) syringes. In administering the composition, the professional opens the bottle and presses the plastic adapter into the opening of the bottle and then attaches the oral syringe to the port of the adapter. Next, the professional may withdraw the dose of medication from the bottle and administer the dose. Then the cap can be replaced on the bottle to be used later. Presently, animal pour-on products generally require administering larger volumes of a composition, thus, the above-described method of administration is not appropriate. Therefore, present pour-on products are either administered in a dosing gun or a dosing cup. Such methods of administration prove difficult to accurately deliver small volumes of medication. Thus, the method of administration of the present invention using the PIBA application system allows for more accurate and convenient administration of the presently claimed pour-on liquid preparation.

The compositions according to the present invention are particularly useful for cattle, bovids, swine, other mammals, and birds. In addition to the treatment of BRD, the compositions of this invention are also suitable for the treatment of other conditions associated with inflammation such as footrot, acute mastitis, pinkeye (infectious keratoconjunctivitis), acute pneumonia, metritis and enteritis in cattle. Also, other inflammatory conditions in other species could be treated with the compositions. The dosage regimen for treatment of such diseases should be appropriate for the species and condition being treated.

Mastitis is a complex disease that occurs in lactating females, and is of particular economic importance in dairy cows and goats. Several pathogenic agents may be involved, including *Staphylococcus aureus, Escherichia coli* and *Streptococcus* species. The acute form of mastitis has a sudden onset, the udder is enlarged, hot to the touch and tender; and usually the affected animal will have a fever. If not treated promptly, the udder may be permanently damaged and milk production may be decreased or lost.

Currently, acute mastitis is treated with antibiotics, anti-inflammatories and oxytocin. The use of the formulations of the present invention would be an improvement by offering a way for animal handlers to safely and conveniently administer flunixin to animals in need thereof to ameliorate inflammation, while minimizing pain and stress to the animal associated with the treatment and the potential for injection site tissue damage. Additionally, the present invention provides an improved method of administrating the formulation because it overcomes the challenges of needle stick hazards and disposal of sharp biowaste material. Moreover, based on the pharmacokinetic data, transdermal flunixin allows for rapid onset of action.

Pinkeye is an acute infectious disease of cattle, sheep and other animals that is characterized by inflammation of the tissues of the eye, accompanied by nasal discharge, lacrimation and copious ocular discharge. Affected animals may display extreme discomfort, resulting in decreased feed intake and subsequent reduction in body weight gain and/or a drop in milk production. In extreme cases, permanent blindness occurs. The disease, which is caused by *Moraxella bovis* in cattle, is widespread, especially among range and feedlot cattle, the cure of which is of great economic importance to the cattle industry.

Footrot (interdigital phlegmon) is an acute infection of the interdigital space that occurs throughout the world in both beef and dairy cattle. *Fusobacterium necrophorum* is the major cause of footrot, although other organisms, including *Bacteroides melaminogenicus*, can be involved. The major symptoms include pain, severe lameness, fever, anorexia, and reduced milk production. Currently, footrot is treated by antibiotic therapy. Recommended therapy can involve treatment for up to five days. The use of the formulations of the present invention would be a useful adjunct therapy because the NSAID would reduce the inflammation caused by footrot and make the animal feel better.

EXAMPLES

The materials and methods of the present invention are further illustrated by the examples which follow. These examples are offered to illustrate, but not to limit the claimed invention.

Some particular transdermal formulations in accordance with the present invention are set forth below.

Formulation A

| Ingredient | Percent w/v |
| --- | --- |
| Flunixin meglumine | 8.3 |
| Menthol | 10.0 |
| 2-pyrrolidone | 35.0 |
| Monothioglycerol | 1.0 |
| Xylene | qs AD |

Formulation B

| Ingredient | Percent w/v |
| --- | --- |
| Flunixin meglumine | 8.3 |
| Menthol | 10.0 |
| 2-pyrrolidone | 35.0 |
| Monothioglycerol | 1.0 |
| D-limonene | qs AD |

Formulation C

| Ingredient | Percent w/v |
| --- | --- |
| Flunixin meglumine | 8.3 |
| Menthol | 10.0 |
| Isopropyl myristate | 25.0 |
| Monothioglycerol | 1.0 |
| 2-pyrrolidone | qs AD |

Formulation D

| Ingredient | Percent w/v |
| --- | --- |
| Flunixin meglumine | 8.3 |
| Menthol | 10.0 |
| 2-pyrrolidone | 20.0 |
| Isopropyl myristate | 20.0 |
| Monothioglycerol | 1.0 |
| Isopropyl alcohol | qs AD |

EXAMPLES

Example 1

| Ingredient | Percent (w/v) |
| --- | --- |
| flunixin meglumine | 16.6% |
| 2-pyrrolidone | 35.0% |
| Menthol | 10.0% |
| isopropyl myristate | 10.0% |
| isopropyl alcohol | qs AD |
| Monothioglycerol | 1.0% |

In order to prepare the composition of the present invention, the vehicle(s) or a portion of the vehicle(s), are added to the compounding vessel, followed by the remaining excipients and the actives. The combination is mixed until all solids are dissolved. Although not included herein, additives, such as those mentioned in the detailed description, are also included in the vessel and mixed into the formulation. The order of addition was not critical.

Example 2

Pharmacokinetics of Flunixin in Product Described in Example 1

The Formulation of Example 1 was assessed in a pharmacokinetic study involving 6 cattle which received a single transdermal application of 1 mL/20 kg (5 mg/kg flunixin). Blood samples for determination of flunixin concentration were collected at 0, 0.5, 1, 1.5, 2, 3, 4, 6, 8, 24 and 48 hours after dosing. The results are shown in FIG. 1, in comparison to IV dosing of Banamine® at 2.2 mg/kg. This study provided evidence that the pharmacokinetic profile of the formulation from Example 1, when dosed at 5 mg/kg flunixin, is similar to that of the IV dosing of Banamine® at 2.2 mg/kg.

Example 3

| Excipient | Conc (% w/v) |
| --- | --- |
| Flunixin Meglumine | 16.60% |
| 2-Pyrrolidone | 35.00% |
| Isopropyl Alcohol | 8.00% |
| Benzyl Alcohol | 20.0% |
| Menthol | 10.0% |
| Propylene Glycol | 10.0% |
| Dicaprylate/Dicaprate | |

The procedure to prepare the composition herein was the same as that done in Example 1.

Example 4

Pharmacokinetics of Flunixin in Product Described in Example 3

Figure 2:
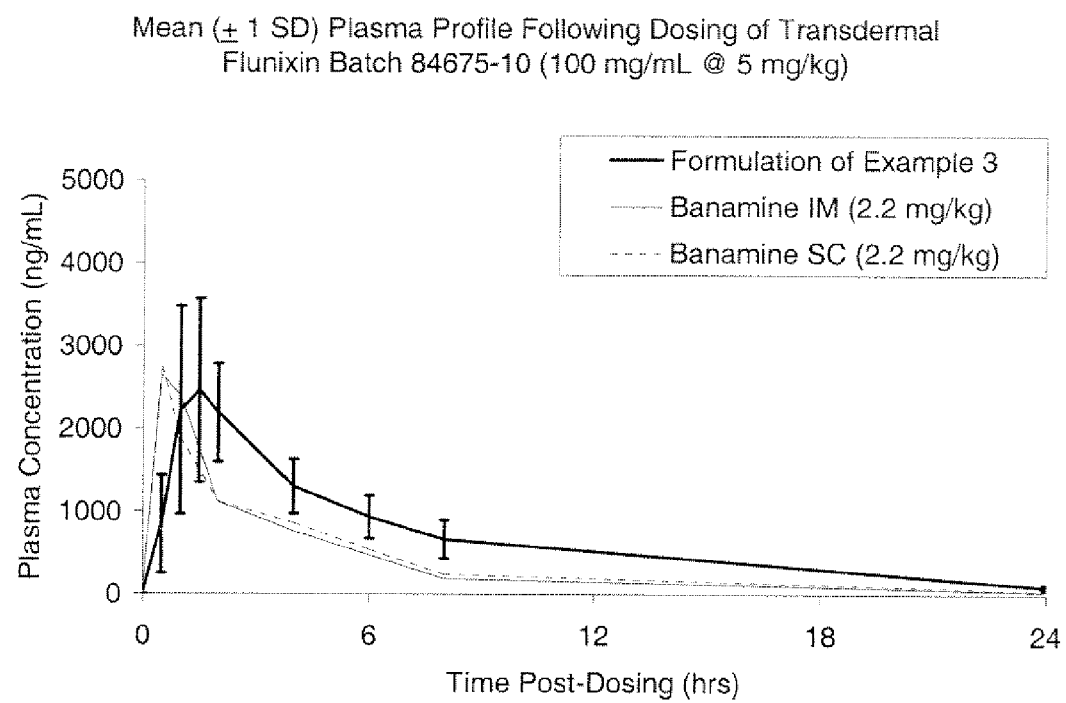
FIG. 2 is a graph showing the results of the tests carried out in Example 4, in which the mean plasma concentration of flunixin (free acid) vs. time after a single 2.2 mg/kg intramuscular (IM, solid line) or subcutaneous (SC, dotted line) dose of Banamine® (flunixin meglumine) is compared to a single 5 mg/kg transdermal dose of composition of the present invention (±1 SD, squares connected by solid line).

The Formulation of Example 3 was assessed in a pharmacokinetic study involving 4 cattle which received a single transdermal application of 1 mL/20 kg (5 mg/kg flunixin). Blood samples for determination of flunixin concentration were collected at 0, 0.5, 1, 1.5, 2, 4, 6, 8, and 24 hours after dosing. The results are shown in FIG. 2, in comparison to intramuscular (IM) or subcutaneous (SC) dosing of Banamine® at 2.2 mg/kg. This study demonstrated that the pharmacokinetic profile of the formulation from Example 3, when dosed at 5 mg/kg flunixin, is similar to that of the IM or SC dosing of Banamine® at 2.2 mg/kg.

Example 5

| Excipient | Purpose | Conc (% w/v) | Conc (% w/v) | Conc (% w/v) |
|---|---|---|---|---|
| Flunixin Meglumine | Active | 8.3% | 8.3% | 8.3% |
| 2-Pyrrolidone | Solvent | 35.0% | 35.0% | 35.0% |
| Menthol | Penetration | 10.0% | 10.0% | — |
| Crodamol CAP | Penetration | — | — | 10.0% |
| Xylene | Penetration | Qs | — | — |
| D-Limonene | Penetration | — | — | Qs |
| Isopropyl Alcohol | Vehicle | — | — | 10.0% |
| DEGMEE | Solvent | 15.0% | qs | 15.0% |
| Methyl Paraben | Preservative | 3.0% | 3.0% | 3.0% |
| Monothioglycerol | Anti-oxidant | 1.0% | 1.0% | 1.0% |

The procedures to prepare the compositions herein were the same as that done in Example 1.

Example 6

Pharmacokinetics of Flunixin in Products Described in Example 5

Figure 3:
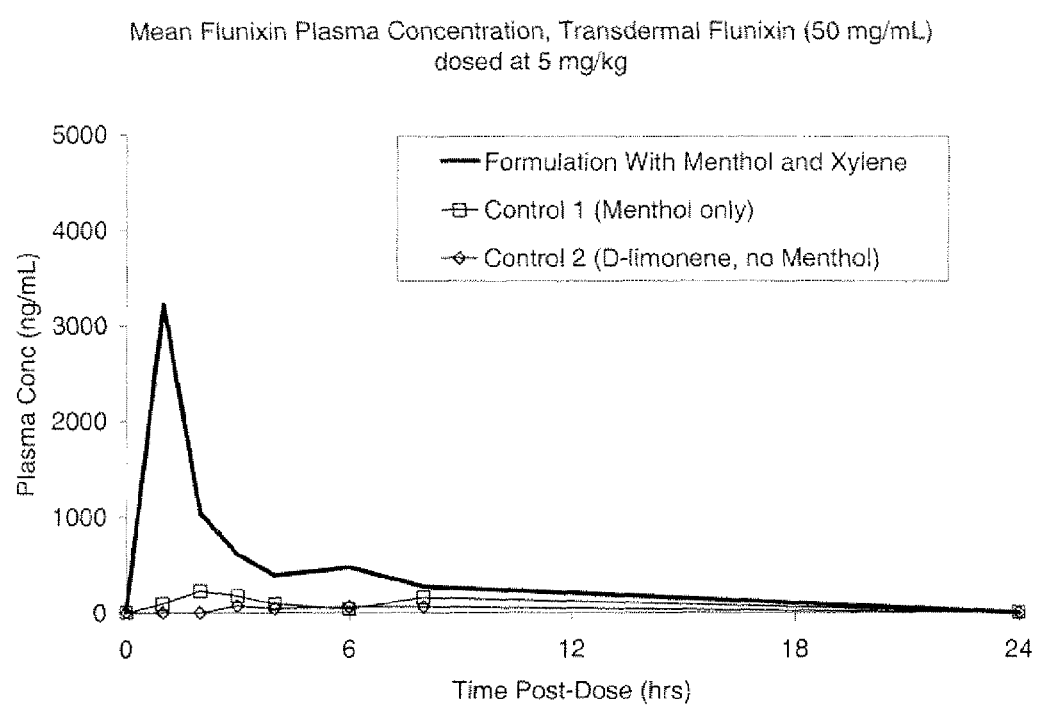
FIG. 3 is a graph showing the results of tests carried out in the experiment described in Example 6 wherein the mean flunixin (free acid) plasma concentration data is shown following dosing of 3 different flunixin meglumine transdermal formulations at 5 mg/kg to show some differences with different dermal penetration enhancers.

The Formulations of Example 5 were assessed in a pharmacokinetic study involving 6 cattle, each of which received a single transdermal application of 1 mL/20 kg (5 mg/kg flunixin). Blood samples for determination of flunixin concentration were collected at 0, 0.5, 1, 1.5, 2, 4, 6, 8, and 24 hours after dosing. The results are shown in FIG. 3. FIG. 3 demonstrates that the plasma uptake of flunixin was enhanced when menthol is used in combination with another penetration enhancer.

Example 6 thus demonstrates the discovery that the combination of the first and second dermal penetration enhancers of the invention provides a synergistic increase in the systemic availability of flunixin meglumine compared to the use of a single penetration enhancer alone.

Example 7

Efficacy of Transdermal Flunixin in Naturally-Occurring Bovine Respiratory Disease The Formulation of Example 3 was evaluated in a study to determine the antipyretic efficacy of different doses in naturally-occurring bovine respiratory disease (BRD). One-hundred twenty (120) beef calves exhibiting signs of acute BRD and with rectal temperature≥104.5° F. were selected. All 120 calves were treated with an approved antimicrobial for BRD (subcutaneous injection of Nuflor® at 2 mL/15 kg body weight) and randomly assigned to transdermal treatment with one of two doses of the Formulation described in Example 3 or with a placebo Formulation that contained no flunixin, but had all of the excipients used in the Formulation of Example 3:

| Group | Number of Calves | Flunixin Active Concentration | Flunixin Dose Rate | Dose Rate Volume |
|---|---|---|---|---|
| A | 40 | 100 mg/mL | 5 mg/kg | 1 mL/20 kg |
| B | 40 | 100 mg/mL | 2.5 mg/kg | 1 mL/40 kg |
| C | 40 | 0 mg/mL (placebo) | N/A | 1 mL/20 kg |

Figure 4:
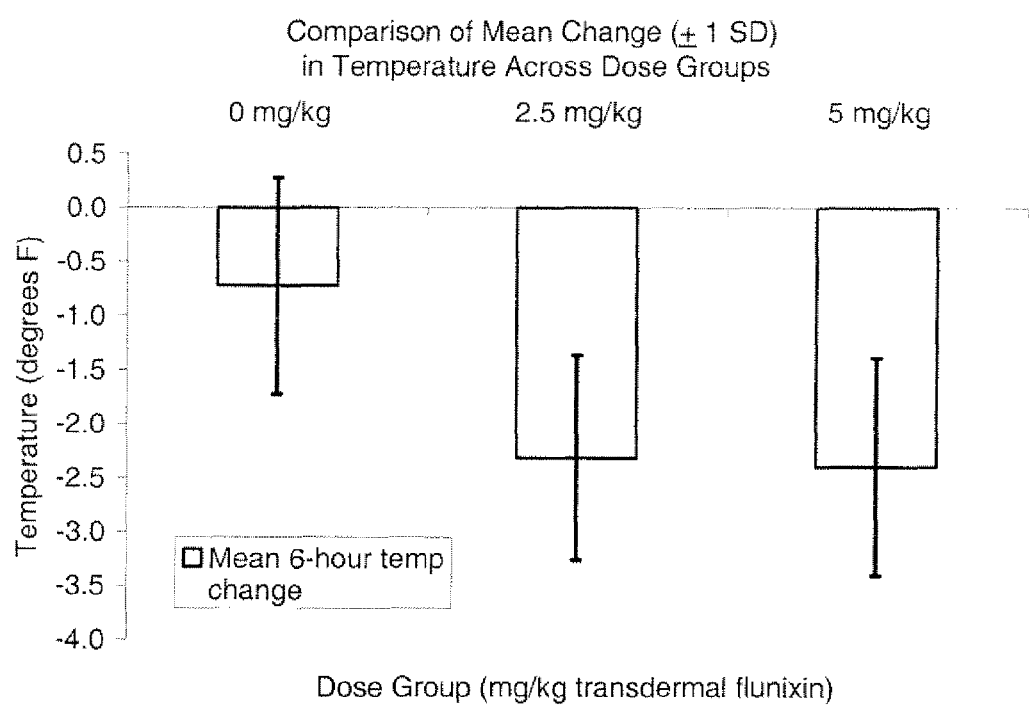
FIG. 4 is a graph showing the results of tests carried out in the experiment described in Example 7 wherein the antipyretic efficacy of transdermal flunixin meglumine (free acid) in naturally-occurring bovine respiratory disease is shown. The mean temperature change (±1 SD) following treatment with an antimicrobial plus transdermal flunixin at 0 mg/kg (placebo), 2.5 mg/kg, or 5 mg/kg is shown.

At six hours following treatment, the rectal temperature of calves was assessed again. The changes in rectal temperature for each group of calves are summarized in FIG. 4. Example 7 thus demonstrates the discovery that a transdermal flunixin dose using the Formulation described in Example 3 at a transdermal dose of 2.5 mg/kg or 5 mg/kg leads to a greater decrease in rectal temperature at 6 hours following dosing than that observed with placebo treatment.

Example 8

| Excipient | Conc (% w/v) |
|---|---|
| Flunixin Meglumine | 16.6% |
| 2-Pyrrolidone | 35.0% |
| Isopropyl Alcohol | 12.8% |
| Benzyl Alcohol | 20.4% |
| L-Menthol | 10.0% |
| Propylene Glycol Dicaprylate/Dicaprate | 10.0% |

The procedure to prepare the composition herein was the same as that done in Example 1.

Example 9

Pharmacokinetics of Flunixin in Product Described in Example 8

The Formulation of Example 8 was assessed in a pharmacokinetic study involving 6 cattle which received a single transdermal application of 1 mL/40 kg (2.5 mg/kg flunixin). Following dosing, animals were maintained in headgates to prevent any licking of their own or their penmates' application sites. Blood samples for determination of flunixin concentration were collected at 0, 0.25, 0.5, 0.75, 1, 1.5, 2, 4, 6, 8, and 24 hours after dosing. The results are shown in FIG. 5. These plasma data were used to estimate bioavailability based on data generated for IV dosing (2.2 mg/kg) of Banamine® (SPRI SN 06482). This study demonstrates that the flunixin detected in the plasma of study subjects is attributable to transdermal absorption. It also generates a bioavailability estimate of greater than 50% for the transdermal formulation presented in Example 8.

We claim:
1. A transdermal liquid preparation for administration to cattle comprising:
   a) a first and a second dermal penetration enhancer;
   b) an aprotic primary solvent; and
   c) a therapeutically effective amount of flunixin meglumine;
   wherein the first dermal penetration enhancer is menthol;
   the second dermal penetration enhancer is a mixture of saturated or unsaturated fatty acid esters or diesters of propylene glycol and glycerol; wherein the first dermal penetration enhancer comprises from about 2 to about 20% w/v of the transdermal liquid preparation; and
   the aprotic primary solvent is 2-pyrrolidone.

2. The transdermal liquid preparation of claim 1, wherein the first dermal penetration enhancer comprises from about 5 to about 15% w/v of the transdermal liquid preparation.

3. The transdermal liquid preparation of claim 1, wherein the second dermal penetration enhancer comprises from about 2 to about 50% w/v of the transdermal liquid preparation.

4. The transdermal liquid preparation of claim 1, wherein the transdermal liquid preparation comprises from about 1 to about 20% by wt of flunixin active.

5. The transdermal liquid preparation of claim 1, wherein the aprotic primary solvent comprises from about 5 to about 90% by wt of the transdermal liquid preparation.

6. The transdermal liquid preparation of claim 1, further comprising a second vehicle or solvent comprising up to about 80% by wt of the transdermal liquid preparation.

7. The transdermal liquid preparation of claim 6, wherein the second vehicle or solvent is water, ethanol, isopropanol, 1,2-propanediol, glycerin, benzyl alcohol, dimethylisosorbide, triacetin, propylene glycol, glycol ethers, ethyl lactate and/or mixtures thereof.

8. The transdermal liquid preparation of claim 7, wherein the glycol ether is selected from the group consisting of ethylene glycol monoethyl ether, diethylene glycol monoethyl ether, and/or dipropylene glycol monoethyl ether.

9. The transdermal liquid preparation of claim 1, further comprising a second pharmaceutically active compound.

10. The transdermal liquid preparation of claim 9, wherein the second pharmaceutically active compound is selected from the group consisting of antimicrobials, anti-inflammatory agents, oxytocin, hormones for reproduction, growth enhancement compounds, physiologic intervention compounds, anxiolytic compounds, antihistamines, immune stimulants, and vaccines.

11. A transdermal liquid preparation of claim 1, comprising:
   a) from about 5% to about 15% by wt of said first dermal penetration enhancer;
   b) from about 2% to about 50% by wt of said second dermal penetration enhancer;
   c) from about 5% to about 15% of said flunixin based on free acid content;
   d) from about 5% to about 90% of said aprotic primary solvent; and
   e) up to about 80% of a second vehicle or solvent.

12. A method of treating inflammatory conditions, comprising administering an effective amount of a transdermal liquid preparation of claim 1 to an animal in need thereof.

13. The method of claim 12, wherein the amount of flunixin administered is from about 1 to about 5 mg/kg active content.

14. The method of claim 12, further comprising administering a second pharmaceutical agent to said animal in need thereof.

15. The method of claim 14, wherein the second pharmaceutical agent is selected from the group consisting of antimicrobials, anti-inflammatory agents, oxytocin, hormones for reproduction, growth enhancement compounds, physiologic intervention compounds, anxiolytic compounds, antihistamines, immune stimulants, and vaccines.

16. A method of administering the transdermal liquid preparation of claim 1 comprising
   a) incorporating said transdermal liquid preparation into a press-in bottle application device, and
   b) administering an effective amount of said transdermal liquid preparation to an animal in need thereof.

17. The transdermal liquid preparation of claim 1, wherein the propylene glycol diester is propylene glycol dicaprylate/dicaprate.

* * * * *